(12) United States Patent
Husemann et al.

(10) Patent No.: US 7,757,019 B2
(45) Date of Patent: Jul. 13, 2010

(54) MOBILE HUB AND MANAGING EVENTS IN A MOBILE HUB

(75) Inventors: Dirk Husemann, Adliswil (CH); Michael E. Nidd, Kilchberg (CH); Jonathan T. Waddilove, Shaftesbury (GB)

(73) Assignee: International Business Machines Corporation, Armonk, NY (US)

( * ) Notice: Subject to any disclaimer, the term of this patent is extended or adjusted under 35 U.S.C. 154(b) by 436 days.

(21) Appl. No.: 11/420,473

(22) Filed: May 25, 2006

(65) Prior Publication Data

US 2006/0242295 A1    Oct. 26, 2006

(51) Int. Cl.
*G06F 3/00* (2006.01)
(52) U.S. Cl. .................... 710/45; 370/468; 713/502
(58) Field of Classification Search .................... 710/45
See application file for complete search history.

(56) References Cited

U.S. PATENT DOCUMENTS 5,850,388 A * 12/1998 Anderson et al. .......... 370/252
6,023,732 A * 2/2000 Moh et al. ................. 709/232
6,161,141 A * 12/2000 Dillon ....................... 709/230
6,886,141 B1 * 4/2005 Kunz et al. ................ 716/1
7,154,903 B2 * 12/2006 Sivalingham .............. 370/429

FOREIGN PATENT DOCUMENTS

EP    1326288 A2    9/2003

OTHER PUBLICATIONS

"Connect With Style". IXI Mobile Inc. Headquarters, pp. 1-13. (Copyright 2001, 2002).

* cited by examiner

*Primary Examiner*—Henry W. H. Tsai
*Assistant Examiner*—Elias Mamo
(74) *Attorney, Agent, or Firm*—Ido Tuchman; Kenneth R. Corsello

(57) ABSTRACT

A mobile hub is proposed, the mobile hub includes a circular buffer for storing events, a timer for monitoring the storage period of an event stored in the buffer, and an event manager designed for discarding an event from the buffer when a time-out of the associated timer is exceeded. As no event can block the buffer any more a small-scale buffer can be used for the mobile hub.

22 Claims, 5 Drawing Sheets

MOBILE HUB AND MANAGING EVENTS IN A MOBILE HUB

BACKGROUND OF THE INVENTION

The present invention relates generally to mobile computing devices, and more specifically, to a mobile hub and techniques for managing events in a mobile hub.

The concept of personal mobile gateways or personal mobile hubs revolves around the concept of a mobile device typically having a central processing unit CPU, a random access memory RAM, a non volatile (NV) storage, an interface to a local wireless network technology (e.g., Bluetooth) and/or an interface to a wireless wide area network technology (e.g., GSM/GPRS).

An attractive application area of mobile hubs is the health care/medical/pharmaceutical application area where sensor and actuator devices connect via, for example, Bluetooth to the mobile hub. Each sensor periodically transmits a sensor value to the mobile hub or is polled by an adapter running on the mobile hub. Actuator devices similarly receive instructions from the mobile hub device from time to time by polling the mobile hub or by being connected by an adapter running on the mobile hub. On the mobile hub the sensor data needs to be analyzed, perhaps correlated to data of other sensor devices, and might also be relayed to network based services. Typically, the data is of a discrete nature, and each sensor value can be treated as an event. Thus, each sensor submits a sequence of events via the wireless communication link to the mobile hub. Likewise, mobile hub internal processes can generate events. Of course, it might be necessary to make these internally created events or the events received from external devices available to consumers on the mobile hub and/or even mobile hub external services. Thus, for handling events and distribute them the right way, the mobile hub needs an event engine, also called event manager.

Event systems as such have been known for quite some time now. There are synchronous event systems and asynchronous event systems. In synchronous event systems, events are propagated along a hierarchical path from the leaves up to the root. Each entity operates on a received event in turn.

One of the best-known examples of asynchronous event systems is the Linda Tuplespace system or IBM's T-Spaces. There, events are posted to a central "blackboard", which is implemented as a database, by event sources. Event consumers then search through the blackboard specifying patterns or search expressions for the tuples they are interested in.

The main advantage of synchronous event systems is that each registered entity (entities have to register) is guaranteed to be called once. At the end of the invocation chain one knows for sure that a certain event has been dealt with. Also, the synchronous event system by definition imposes a certain order in which registered events are called: By using appropriate return values, it is possible to influence delivery of events to entities later in the processing chain. This advantage of the synchronous model is at the same time its biggest disadvantage: Input/Output (I/O) operations, for example, can take a long time to complete. An entity whose event handler is invoked and initiates an I/O operation as part of the event handler might consequently become blocked and, thus, block the whole synchronous event system. Also, the event handling entity might become blocked before being invoked, and thus, can also block the event system.

Asynchronous event systems do not suffer from this particular problem: Here, all event listeners are either informed on the new event simultaneously or interested entities regularly poll the event system for newly arrived events themselves. On the other hand, with asynchronous event systems it is rather difficult to state event closure, i.e. that all entities have seen the event, and almost impossible to enforce an order. Also, with tuple/blackboard based systems, there is a problem of having to support a database and of having to do garbage collection on the posted events.

Hence, asynchronous event systems can be characterized as soup model or pond model. Events are dumped into a global soup or pond. Event subscribers then search the soup/pond. Likewise, synchronous event systems can be characterized as a flash model. An event is flashed to all subscribed entities.

Mobile devices such as mobile hubs, that can for example be a mobile phone platform with a wireless wide area network component (WWAN, e.g., GPRS), a wireless local area network component (WLAN, e.g., Bluetooth), and a CPU with local volatile and non-volatile storage, are characterized by their hub nature. External entities such as sensors, devices or appliances connect via the WLAN to the mobile hub and provide data to software components running on the hub. These or other software components process the received data in some way and then provide data via the WWAN to services running somewhere in the Internet.

Synchronous event systems are unsuitable to perform the processes required for a mobile hub due to the inherent I/O operations that have to be carried out. Asynchronous event systems on the other hand are not particular useful either, as they require a database system to be maintained on the mobile device itself. Such a database would require a lot of resources on a mobile device that typically is characterized by providing scarce resources due to its portable properties.

BRIEF SUMMARY OF THE INVENTION

The present invention presents an event management system that is suitable for mobile devices and simultaneously able to deal with the complexities introduced by blocking I/O operations.

According to one aspect of the present invention, there is provided a mobile hub, including a circular buffer for storing events, a timer for monitoring the storage period of an event stored in the buffer, and an event manager designed for discarding an event from the buffer when a time-out of the associated timer is exceeded.

According to another aspect of the invention, there is provided a corresponding method for managing events in a mobile hub, including the steps of storing an event in a circular buffer, monitoring a storage period of a stored event, and discarding the event from the buffer when the storage period exceeds a time-out.

The mobile hub represents a mobile device that is used as a central device interconnecting entities that are connected to the mobile hub in a wireless fashion. The mobile hub thus accepts the function of a mobile network node. The functions of a mobile hub can e.g. be implemented in a stand-alone device, or be integrated into a mobile phone.

External entities can connect or be connected to the mobile hub and deliver or receive data. Examples of such entities are sensors or actuators. Messages received by the mobile hub are called "events" in the context of the invention.

The core of a mobile hub is called event engine or event manager. The event manager can be implemented in hardware or in software or in a combination of hardware and software. This event manager is designed for handling events in the mobile hub, and in particular for reacting on arriving events and/or for communicating events to the hub's outside world.

Events are typically posted to the event engine by adapters which will be explained later in more detail. The event manager stores the event in a small, limited, temporary buffer and sets up a timer for the event. The starting point of the timer is preferably the point in time when the event is stored in the buffer but need not necessarily be. The timer can be implemented in hardware or in software or in a combination of hardware or software. The event manager discards the event from the buffer at the latest when the timer exceeds a time-out. When the event is already discarded before the time-out of the timer is reached as will be shown in some preferred embodiments of the invention, then the timer will typically be reset and does not reach the time-out anyway.

This sort of event handling ensures, that an event cannot block the limited buffer cells for other events that have to be handled by the event manager. As a consequence, an event can only be present and stored in the buffer for a maximum time/storage period which is determined by the timer's time-out.

An event might be stored in the buffer immediately after arriving at the mobile hub. Alternatively, the event might first be stored temporarily at a temporary storage or a cache and afterwards transferred to the circular buffer. The circular buffer provides limited space for storing events. In one preferred embodiment, less than 200 events can be stored in the circular buffer, in another preferred embodiment less than 100 events, in yet another preferred embodiment the size of the circular buffer can be configured depending on the application.

As indicated above, the time-out of the timer is preferably the latest point in time to discard a stored event from the buffer. According to a preferred embodiment, together with or a short time before or after storing an event in the buffer and starting the corresponding timer, the event engine notifies all or selected entities of the arrival of the event. However, the notification of registered entities can also go along with the arrival of the event at the mobile hub, and not necessarily with the arrival of the event in the buffer, or with any other action related to this event. The notification preferably comprises the event. If entities should only selectively be notified, the event manager notifies all entities according to a registration list. Entities can register at the registration list to be notified on all or on selected events only. E.g. external entity sensor A registers to be notified upon any event arriving at the mobile hub from sensor B, as a measured value from sensor B should trigger a measurement at sensor A. Entities in general can be external entities and/or mobile hub internal entities. Regardless of the form of an entity, entities that have seen such a notification reply asynchronously with an acknowledgement message ACK. If either all entities that were notified—and that consequently had previously registered with the registration list in order to become notified—have sent an ACK message or else if the timer for this event expired the event manager simply discards the event.

This mechanism prevents the mobile hub from being blocked by stored events where the event engine cannot be sure whether this event already was attended to all interested entities. On the other hand, a database including complex access is not required. Instead, the event manager manages the event circulation in the buffer following fixed rules as stated above and thus, prevents the buffer from being blocked. Hence, the event handling solution is efficient, highly adaptable and extensible. As no event can block the buffer any more, a small-scale buffer can be used for the mobile hub that in turn keeps the mobile hub handy and portable.

The mobile hub is in particular resistant against blocking events when all the stored events comprise a corresponding timer for monitoring the storage period of the associated event. Then, every event resides only a limited maximum time in the buffer that corresponds to the time-out of the associated timer before it will be discarded.

The time-out of a timer can preferably be a variable time-out that depends on an event arrival rate. The more events arrive at the mobile hub per time unit, the shorter the time-out is. The less events arrive at the mobile hub, the longer the time-out can be without deteriorating the performance of the mobile hub.

The time-out can also differ for different applications running on the mobile hub. Then, a limited part of the buffer can e.g. be assigned to a particular application which application can afford a longer time-out due to rarely arriving events, while the remaining part of the buffer is reserved for events belonging to another application with a more frequent arrival rate and thus a shorter time-out. The engine manager can be responsible for classifying events to applications and filling the respective buffer parts accordingly.

The mobile hub preferably comprises hardware elements known in the art. In particular, the mobile hub preferably comprises an interface to a wireless local area network for receiving and/or transmitting events from/to external entities. Such access to a WLAN can e.g. comprise access to a WLAN according to the 802.11 specification, and/or comprise access to Bluetooth. In addition or alternatively, the mobile platform preferably comprises an interface to a wireless wide area network WWAN such as to a GSM, GRPS, or UMTS network. External entities such as sensors, devices or appliances can connect via the WLAN and/or the WWAN to the mobile hub and provide data to software components running on the hub. External devices can also be recipients of data transmitted via the WLAN and/or the WWAN. Hence, external devices can either be event sources or event comsumers or both event sources and event consumers at the same time.

Mobile hub internal entities can be software components as mentioned above. Such internal entities work on events, and can provide a variety of functions. An internal entity might include the function of a router, another internal entity might include the function of a server, and so on. An internal entity processes received events in some way. It can provide processed data via the WWAN to services running somewhere in the Internet.

As the mobile hub internal event representation might be different to an event representation an external entity might be able to process, the mobile hub preferably comprises adapters for converting an internal representation of an event into a representation of the event comprehensible to an external entity and vice versa. Different external entities might require different adapters in the mobile hub.

Further preferred embodiments cover the possibility of annotating events in the system. Events which typically follow a fixed notation scheme can preferably be annotated by entities of the system. This means that preferably internal entities but also external entities can annotate a received event in order to initiate further action. Such event together with the annotation is typically sent back to the event manager of the mobile hub and is handled accordingly. The event manager preferably distributes the annotation to registered entities. Annotating events is an easy and flexible way for enhancing the communication performance of the entire system.

Such annotation can preferably be attached to any event sent to the event manager for proper handling. However, in particular, an acknowledgement message can be the carrier of an annotation added by an entity. It is noted, however, that not only the annotation itself can be distributed. According to another preferred embodiment, the entire event, including the annotation, is distributed by the event manager.

According to another embodiment of the present invention, there is provided an event model wherein the appearance of an event follows an event notation which notation comprises different fields per event, each field specifying a certain category of information. Preferably, at least some of the fields follow a hierarchy. Such an event model facilitates the handling of events inside the mobile hub, as in particular filters for events can be implemented easily.

According to another aspect of the present invention, there is provided a computer program element, which computer program element comprises code means for performing a method according to any one of the method claims when loaded in the processing unit of a mobile hub.

It is noted that in general embodiments of the apparatus as well as advantages of the apparatus and its embodiments are also considered as embodiments of the method respectively as advantages of the method and its embodiments and vice versa.

DETAILED DESCRIPTION OF THE INVENTION

Figure 1:
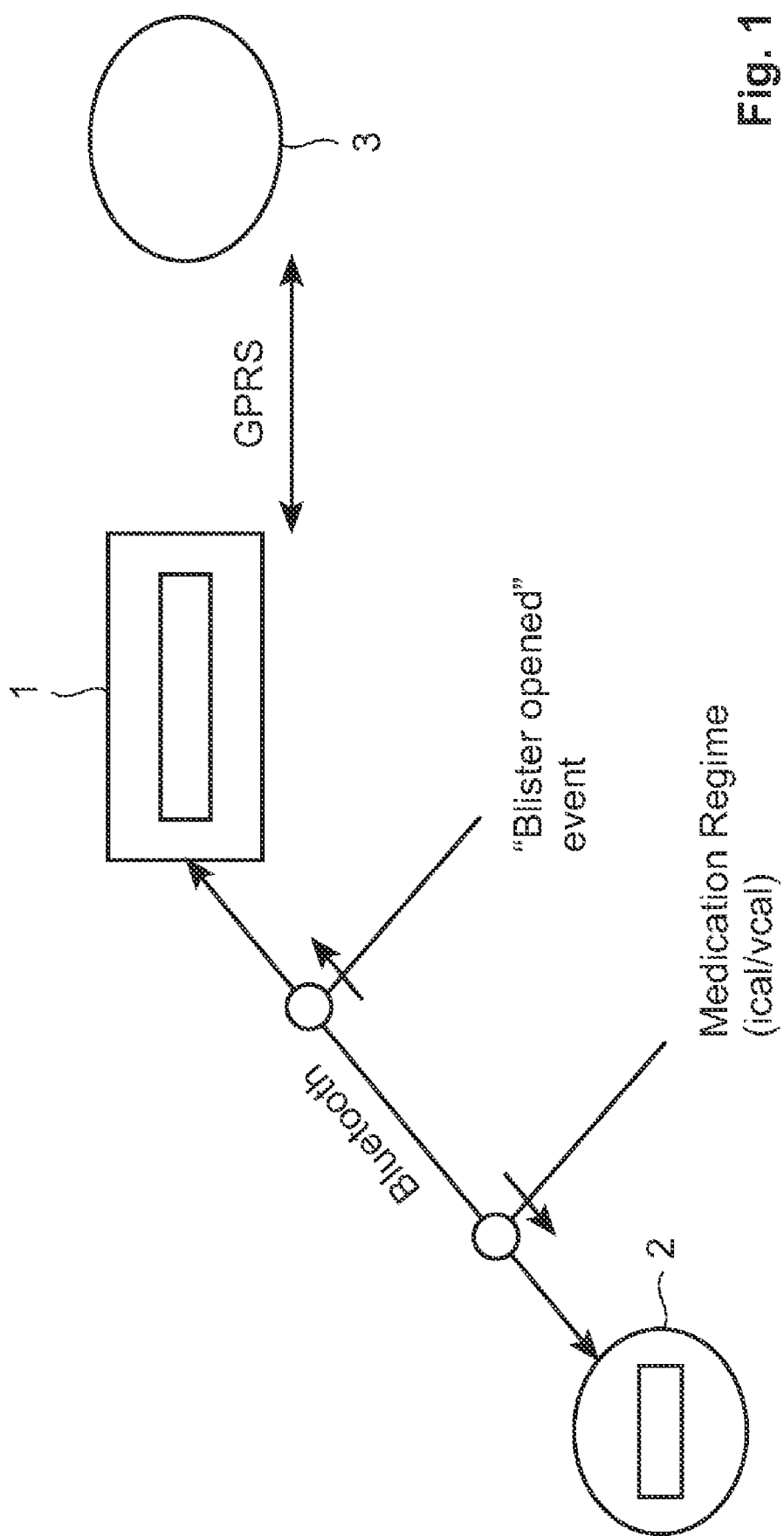
FIG. 1 shows a diagram of a system comprising a mobile hub according to the present invention.

As will be appreciated by one skilled in the art, the present invention may be embodied as a method, system, or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present invention may be written in an object oriented programming language such as Java, Smalltalk, C++ or the like. However, the computer program code for carrying out operations of the present invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

FIG. 1 illustrates a diagram of a system comprising a mobile hub according to the present invention. A typical mobile hub can include a runtime system such as the Symbian OS, or Linux, or a PersonalJava or MIDP Java runtime environment and appropriate WLAN and/or WWAN components.

The mobile hub 1 according to FIG. 1 is actually communicating to two external entities 2 and 3. External entity 2 is a sensor for monitoring medication compliance (the device monitors a blister pack) and is connected to the mobile hub 1 via the wireless local area network Bluetooth. External entity 3 is a server running a remote patient monitoring application and connected to the mobile hub via the wireless wide area network GPRS. A medical administrator (e.g., doctor, nurse, etc.) can set up a medication regime (i.e., how many pills to take when) with the patient monitoring application. The patient monitoring application 3 sends the medication regime (e.g., as an ICAL or VCAL calendar specification) via GPRS to a network adapter running on the mobile hub 1. The network adapter injects the medication regime into the event engine which redistributes it to all registered adapters: one of which is the medication compliance monitor adapter which sends the information (possible converted into a proprietary format or just as is) to the medication compliance monitor via a Bluetooth link. The medication compliance monitor 2 will sound an alarm to the patient once the time to take the medication has been reached. If the patient takes the medication from blister pack contained in the medication compliance monitor 2, the compliance monitor 2 will connect to the mobile hub 2 via Bluetooth and transmit a "blister opened" event (containing the time the blister was opened and possible other information) to the medication compliance adapter on the mobile hub 2. The medication compliance adapter converts the sensor information into a standardized event format and injects it into the event engine, which forwards the event to all other registered adapters. The GPRS network adapter submits the medication event via GPRS to the remote patient monitoring application 3.

As already shown in connection with FIG. 1, the health care/medical/pharmaceutical application area where sensor and actuator devices, collectively called external entities, connect via, for example, Bluetooth to the mobile hub, is an attractive application area of mobile hubs. Each sensor periodically transmits a sensor value to the mobile hub. On the mobile hub the sensor data needs to be analyzed, perhaps correlated to the data of other sensor devices, and might also be relayed to network based services. Typically, the data is of a discrete nature and each sensor value can be treated as an event. Thus, each sensor submits a sequence of events via the wireless communication link to the mobile hub. Likewise, mobile hub internal processes/entities can generate events. Of course, it might be necessary to make these internally created events or the events received from external entities available to consumers on the mobile hub and/or even mobile hub external services. Thus, to efficiently handle events and distribute them appropriately, the mobile hub needs an event engine, also called event manager.

Figure 2:
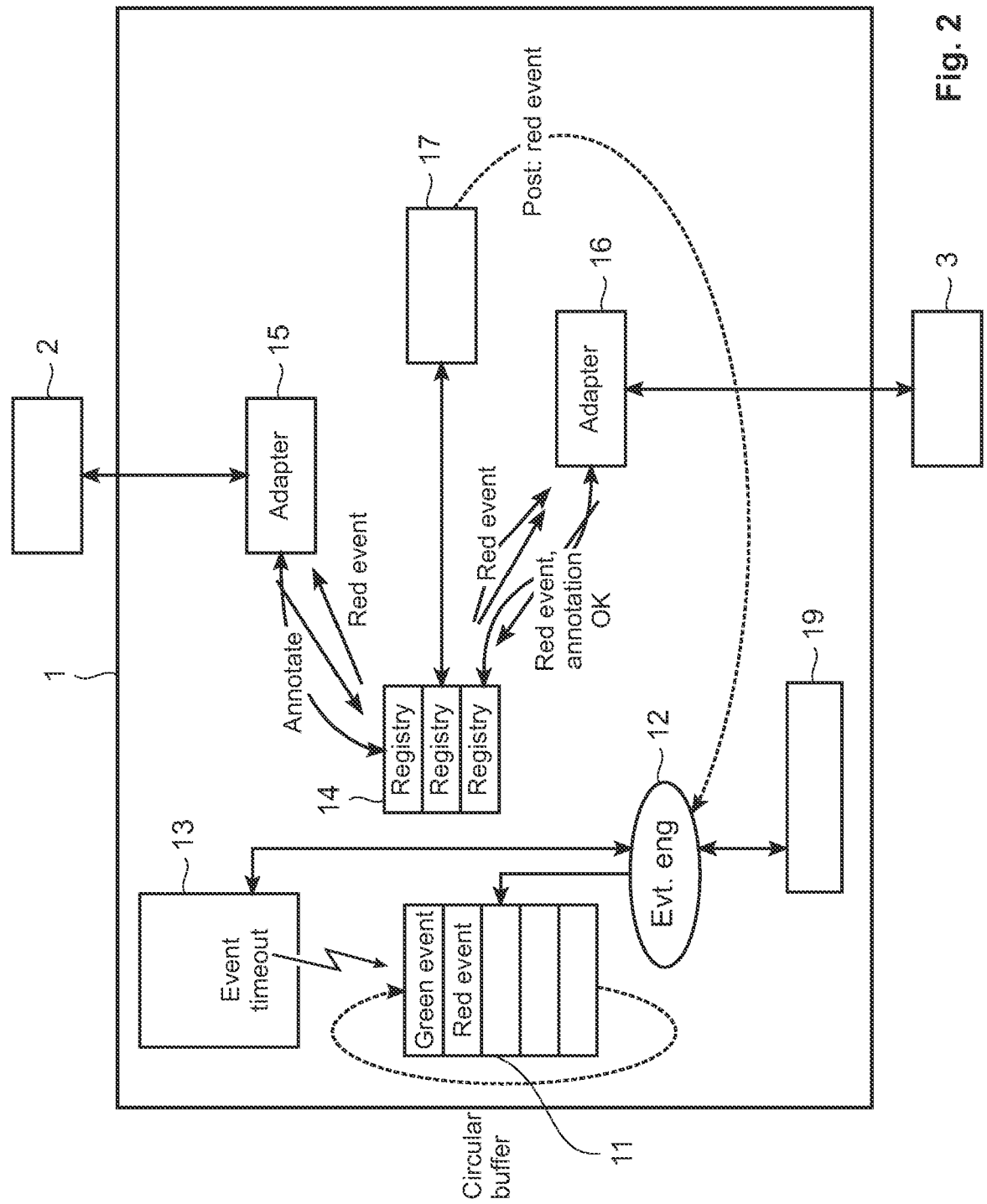
FIG. 2 shows a schematic diagram of a mobile hub, in accordance with an embodiment of the present invention.

FIG. 2 shows schematically how an event engine/event manager is integrated in a mobile hub. The mobile hub 1 according to FIG. 2 comprises a circular buffer 11, an event engine 12, a timer unit 13, a cache 14, adapters 15 and 16 and an internal entity 17.

As the mobile hub according to FIG. 2 can be regarded as an event handling system, events—which are basically messages that trigger a reaction in the system—are the basic information/data bearing carriers. An event can be generated by external entities such as entities 2 or 3 according to FIG. 2. The mobile hub 1 has a need to transform the external representation of an event into a representation that is comprehensible inside the mobile hub. Likewise, an external entity exchanging events with the mobile hub 1 has a need to convert the mobile hub internal representation of an event into a representation that is comprehensible for the external entity. This conversion is the primary job of adapters. As can be derived from FIG. 2, adapters 15 and 16 are located as intermediary between external devices 2 and 3 and the internal event handling system of the mobile hub 1. Adapters generally interact with external entities and mobile hub applications.

However, an event can also be generated, modified, analyzed or worked on by mobile hub internal entities, such as internal entity 17 according to FIG. 2.

Once an event arrives at the mobile hub either submitted from an external entity or created by an internal entity, the event is cached in cache 14. The event manager 12 then transfers event by event to the circular buffer 11. Events are only transferred to the circular buffer once a memory cell of the circular buffer 11 is ready to accept a new event. This event handling requires a mechanism that grants a non-blocking event processing in the circular buffer, as the buffer cannot accept an unlimited number of events due to its limited size.

A mechanism for achieving a buffer 11 with non-blocking properties is the use of timers. In FIG. 2, the timer unit 2 provides a timer for every event actually stored in the buffer 11. For each timer, a time-out is defined. The time-out can be defined in many different ways. A time-out can be defined on basis of an anticipation of events to be handled or events expected to arrive per time unit. The time-out value can also be implemented as variable time-out value that is basically dependent on the arrival rate of events to be handled. According to this latest embodiment, a measurement for measuring the arrival rate can be introduced to the mobile hub.

The time-out basically defines the maximum period of time an event can occupy a memory cell in the buffer 11. By the latest when the time-out for a particular event is exceeded, this particular event is discarded from the buffer in order to have the memory cell released for another event to be handled.

Preferably, the timer is set when the event is stored in the buffer 11. In another embodiment, the timer is set when the event arrives at the mobile hub. While in the first embodiment, an event can occupy the buffer for a fixed time which is the time-out time, the time-out time of the second embodiment defines a maximum stay of an event in the mobile hub, wherein the effective time in the buffer might be little less than the time-out time due to the time needed for handling the event in the mobile hub but outside the buffer.

Basically, the time-out unit 13 provides timers for every event stored in the buffer. The event manager 12 is responsible for storing events in the buffer 11, for setting timers in the timer unit 13, and for discarding events from the buffer 11 when the time-out of the respective timer was exceeded.

However, during the time spent by an event in the buffer, this event should be processed. Subject to the event, the event has to be processed by an internal entity, or has to be processed by an external entity or has to be processed by an internal and external entity. Before processing an event, the event has to be transferred to the processing entity. Therefore, a registration list 19 is established in the mobile hub 1. The registration list 19 provides information, which sort of event has to be communicated whereto. For example, an entry in the registration list 19 might look like: "All events coming from an external sensor have to be sent to the internal agent 17 for further processing" or "All events coming from the internal agent have to be forwarded to the SMS adapter 16 of the mobile hub in order to be communicated via GPRS to an external entity". Entities can register or subscribe with the registration list and indicate in which sort of events they are interested in.

Preferably, the event manager 12 has access to the registration list 19 and handles events accordingly once an event is stored in the buffer 11. Therefore, together with storing an event in the buffer 11, the corresponding timer is set and the event is transmitted to all interested entities according to the registration list 19. It is not necessarily the event itself that is transmitted to such registered entities. In more general words, the registered entities are notified on the event. The notification might be a message not identical or identical to the event that triggered a notification.

A notification is triggered upon the arrival of a new event. In this context, the arrival can be interpreted as arrival in the circular buffer 11, or as arrival at the mobile hub, or as arrival at any time in between. Typically and as indicated in FIG. 2, the notification will be triggered when the event is stored or short time before or afterwards, since the event has to raise the attention of the event manager 12 first which then looks up the registration list 19 for determining the recipients of a notification upon this event.

An implementation of the mobile hub 1 provides a way of returning acknowledgement messages back to the event manager 12—either directly or via the cache 14—upon the receipt of a notification. Thus, the event manager 12 can monitor which entities—internal or external ones—have acknowledged the receipt of a notification. When all the recipients have acknowledged the receipt of the notification, the event that has triggered the notifications is not needed anymore from an event handling point of view. Internal or external entities might take further processing steps in response to the notification. However, in an event based system, if needed these entities simply transmit a new event to the mobile 1 hub for further handling by the event manager 12 once they have to communicate further information to any entity of the interconnected mobile system. Such event will then be handled the same way as described above.

However, an event will only be discarded from the buffer upon receipt of an acknowledgement message ACK from all the notified entities—and thus when the last ACK will be received by the event engine 12—before the time-out of the corresponding timer. As long as not all expected acknowledgments—acknowledgments are expected from the notified entities—are received before the time-out of the corresponding timer will be exceeded, the event is discarded from the buffer upon the timer exceeding its time-out. This prevents the buffer from being blocked by events which recipients of the event related notifications are unable to acknowledge the notification for what reason ever—breakdown, disconnected mode, etc.

There is provided another feature in the mobile hub of FIG. 2. Entities can reply with an event annotation instead of an ACK or with an annotated ACK to augment the stored event. In that case the event manager 12 updates the event stored in the buffer 11 with the annotation, resets the timer for that event and re-notifies all subscribed entities except the one that annotated the event.

Annotating events in general provides the possibility that any entity/subscriber can provide additional data to an existing event—and thus annotate it. The principle behind this annotation mechanism is that all annotations are made available to all other interested entities. This mechanism helps improving the speed of handling events by the event manager. However, the right to annotate cannot only be granted to notified entities. Also adapters could comment on events that pass by, if needed.

According to FIG. 2, there are two events actually stored in the buffer 11: a "green event" and a "red event". The red event was posted by adapter 17 to the event engine 12 (dotted line between 17 and 12). The event engine 12 entertains a registry of adapters 14. The event engine 12 notifies the other subscribed adapters 15 and 16 of the red event. Adapter 16 simply acknowledges the receipt of the red event; adapter 15 annotates the red event and returns that with the acknowledgement to the event engine 12. The event engine 12 redistributes the red event and the annotation to the other adapters, in this case to adapter 16. Adapter 16 again acknowledges the receipts of the annotated event. Once all adapters have acknowledge receipt of the event (and its annotated version) the event engine 12 then can remove the red event from the circular buffer. For the green event an event timeout occurred the event engine removes it from the circular buffer as well then.

Adapters, and also internal entities can provide event filters (e.g., a filter pattern) to indicate their interest in just certain kind of events. The event engine will only forward those events to a specific adapter that matches the filter pattern. Also, the event engine will not add any adapter whose filter pattern did not match an event to the set of notified parties for that particular event. By tuning the time-out parameters and including the current values in the notifications sent by the event engine to adapters the system can be adapted to different usage scenarios and also communicate changes and enable adapters to react.

Figure 3:
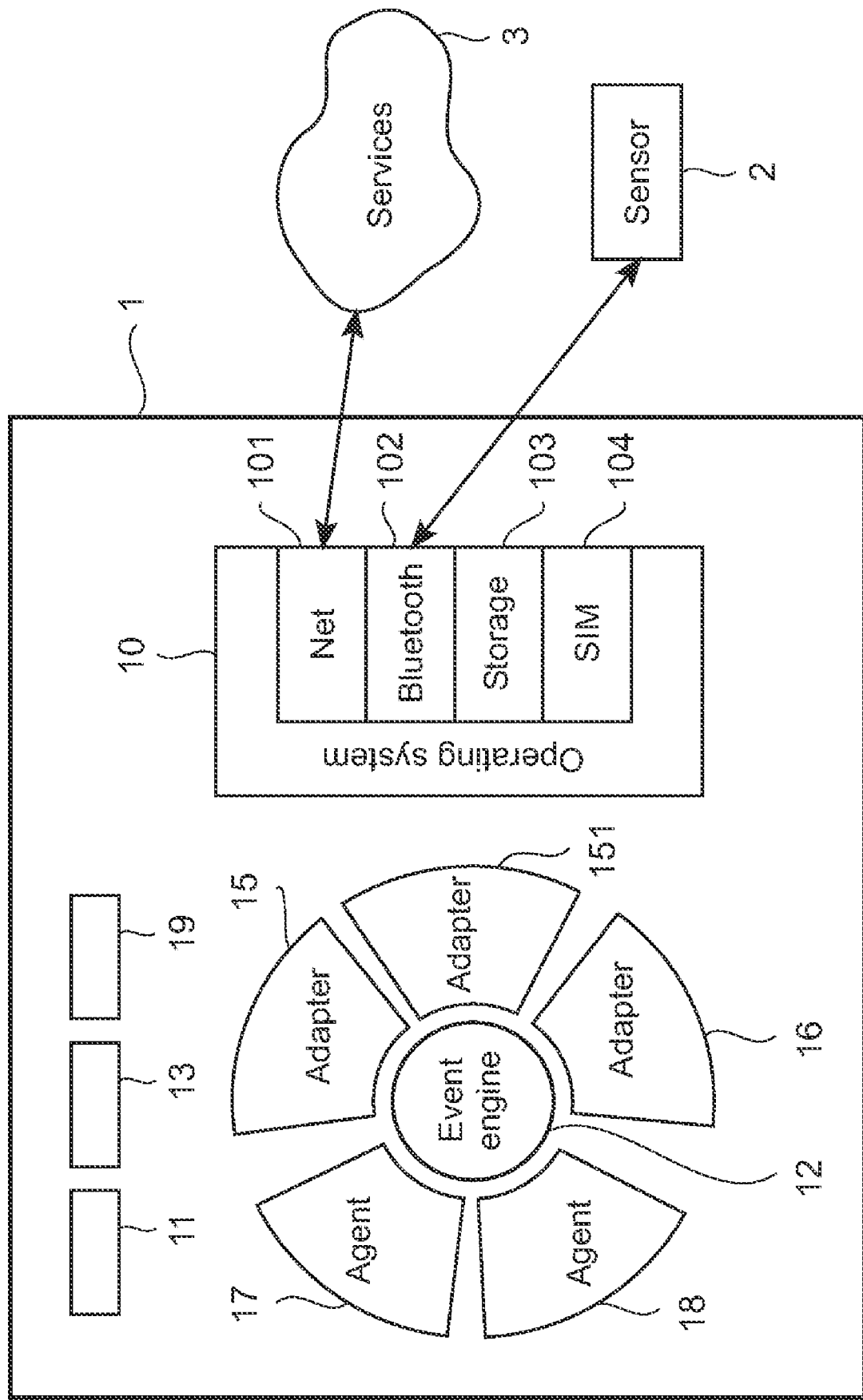
FIG. 3 shows another schematic diagram of a mobile hub, in accordance with an embodiment of the present invention.

FIG. 3 illustrates another mobile hub 1 schematically. Again, an event manager 12 handles events by making use of a circular buffer 11 for temporary storing events. The timer unit 13 provides timers for all stored events, while the registration lists provides information to the event manager 12 which events stored in the circular buffer 11 shall be sent to which interested entities.

There are two internal entities or agents provided, referenced by numbers 17 and 18. There are three adapters 15, 151, 16 provided for supporting communication between external entities and the event manager 12. There are two external entities 2 and 3 visible and connected to the mobile hub 1. External entity 2, which comprises sensors, is connected to the mobile hub 1 via Bluetooth. External entity 3 called "Services" is connect to the mobile hub 1 via a net connection on GRPS. Block 10 indicates the hub's operating system. References 101 to 104 depict elements from a more hardware point of view: Block 101 represents the GRPS interface, block 102 the Bluetooth interface, whereas block 103 represents the storage means of the mobile hub. Block 104 represents the SIM of the mobile hub (SIM=subscriber identity module). As can be derived from FIG. 3, an external device such as external entity 2 is connected to the mobile hub via the Bluetooth interface 102. And there is an adapter assigned to this external device for transforming event notation, which is adapter 15 according to the embodiment of FIG. 3. In general, an adapter can be assigned to an entire interface or alternatively, to a particular entity.

The minimum API set that is required to access the mobile hub comprises instructions such as "register( )" for registering an entity, "deregister ( )" for deregistering an entity, and "post ( )" for posting events.

Exemplary adapters are e.g., one or more of which can be embodied in a mobile hub subject to the configuration and the needs of the hub:

a sensor adapter for interconnecting to one or more sensors;

a persistent storage adapter for interconnecting the mobile hub to a storage device, e.g. for backup purposes;

a HTTP adapter for connecting to Internet Protocol based services;

a debugging adapter for connecting to a diagnosis tool, communication adapters such as WLAN adapter, SMS adapter, etc.

Internal entities can, for example, be embodied as:
a calendar entity;
a alarm entity;
a device discovery entity;
a device monitoring entity;
a data monitoring entity;
a configuration entity.

Figure 4:
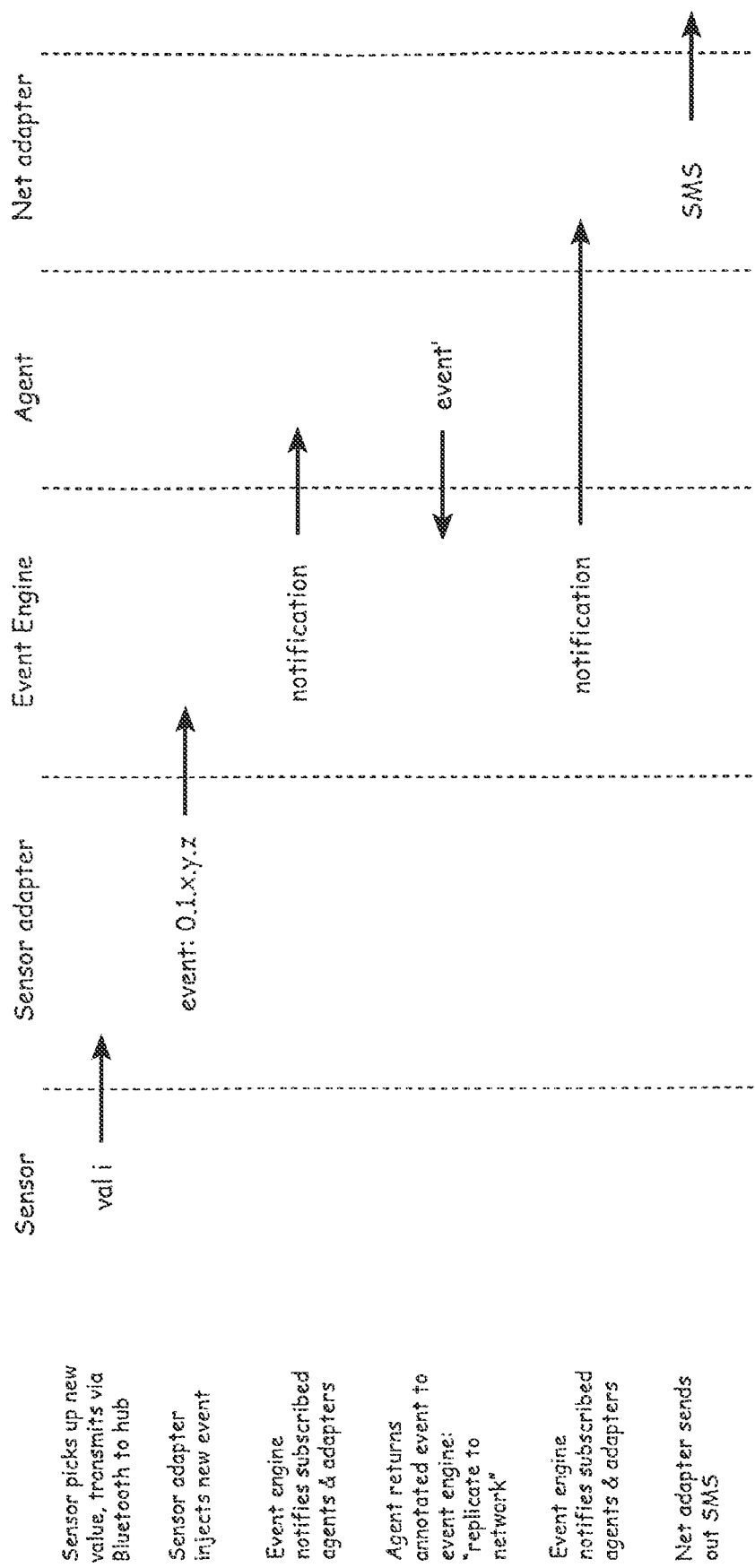
FIG. 4 shows a diagram of example event flows, in accordance with an embodiment of the present invention.

FIG. 4 shows a diagram of example event flows, in accordance with an embodiment of the present invention, with particular focus on the feature of annotating events.

A sensor which, for example, could be the external entity 2 according the diagram in FIG. 2 or FIG. 3 picks up a new value val i and transmits it to the mobile hub via Bluetooth. This message is an event. The corresponding sensor adapter—which could be adapter 15 according to FIG. 2—converts the external representation of the event comprising the value val i into a hub internal representation of the event which representation shall e.g. be event 0.1.x.y.z. Such a notation will be more fully explained with regard to FIG. 5. After the conversion, the event in its new notation is injected by the sensor adapter into the event handling system of the mobile hub.

According to a registration list, for example, the registration list 19 according to FIG. 2, the event manager notifies subscribed entities, for example, agents and adapters. Upon such a notification agent 17 of the mobile hub according to FIG. 2 returns the event, here the notification is identical to the event, together with an annotation to the event manager. The annotation shall express that the "event should be replicated to the network", as the agent might have stated that the event is of interest to the network. As the annotation explicitly indicates an addressee, the registration list might provide an entry such as "if an event or an annotation explicitly provides an addressee, the interested entity is only this addressee" in order to enable appropriate notification. Hence, the event engine notifies the subscribed entities which in this case are only the GSM/GPRS adapter. Thus, the event engine sends the event to the corresponding net adapter that could be adapter 16 according to FIG. 2. Net adapter 16 then converts the event into an SMS (short message service) and sends the SMS out.

Figure 5:
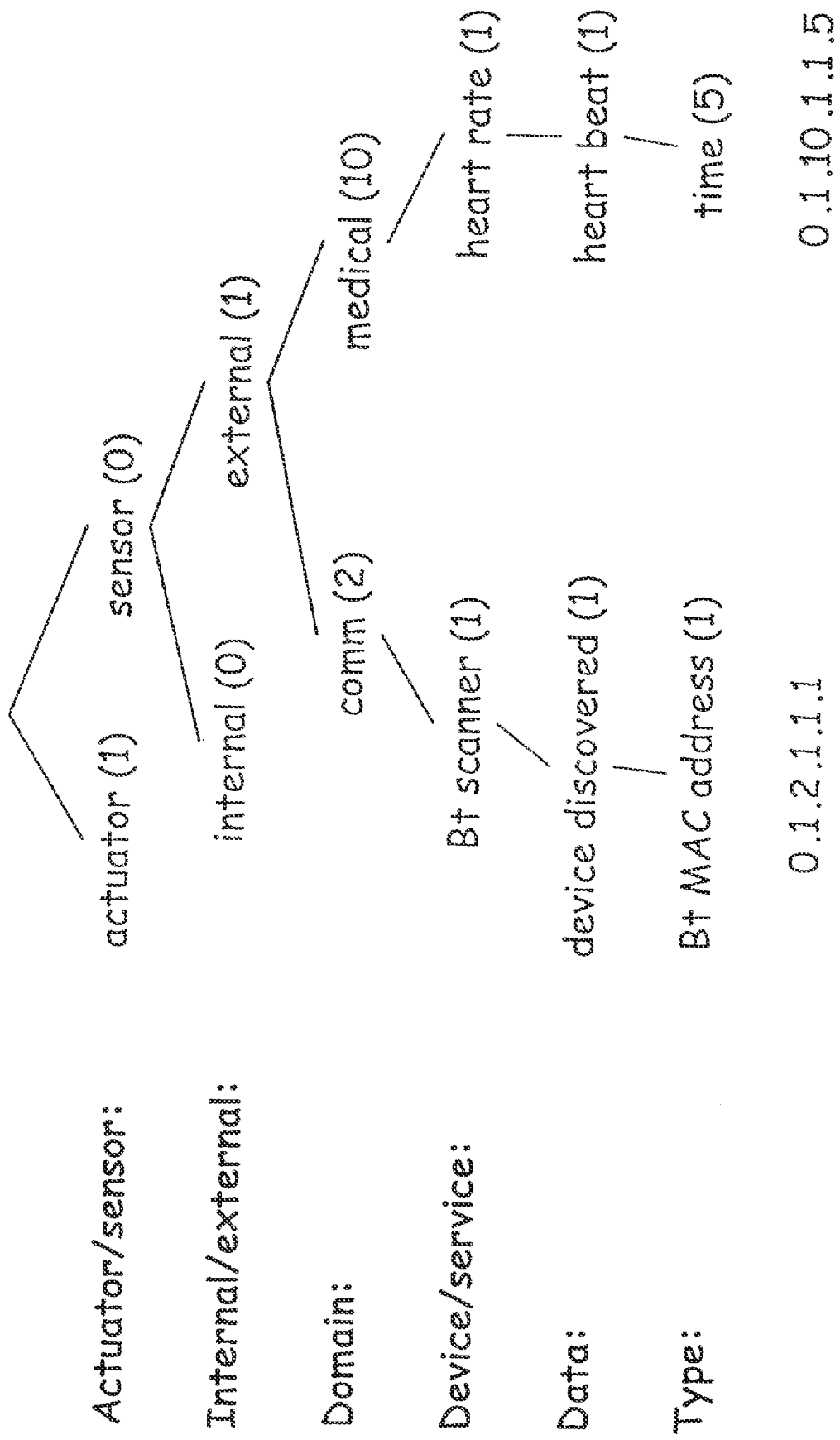
FIG. 5 shows an event structure, accordance with an embodiment of the present invention.

FIG. 5 shows an event structure that is reflected in a corresponding event notation. Thus, a taxonomy for categorizing events is introduced. According to the model, on a first level, events are distinguished between sensor and actuator events. Sensor events report data to the system. For example, a temperature sensor posts temperature measurements, a GSM sensor reports an incoming phone call and the caller ID, a heart rate sensor reports a heartbeat, and so forth. Actuator events in turn request an action to occur. Actuator events indicate commands. For example, a store event would signal that the attached data element should be stored somewhere, a GSM phone call event would indicate that a GSM phone call should be started. According to FIG. 5, the first digit of an event notation indicates whether the event is a sensor event or an actuator event, wherein the sensor event class of events mentioned is indicated by a (0) in the first digit, and the actuator event class is indicated by a (1) in the first digit.

Aside from the top level differentiation between sensor and actuator events, there are provided second level event categories for the event source, third level categories for domains, and fourth level categories for sensor/actuators An event source can be an external or an internal one—always in relation to the mobile hub. The domain can indicate what the event relates to, such as to the system in general, the phone subsystem, a medical domain, an automotive domain, etc. The sensor/actuator classification uses the terms sensor and actuator in the widest possible meaning: A sensor can be a device that just provides a single bit of information but can also something quite complex, likewise an actuator can take a single bit of information and act on it or it can take a complex set of instructions.

Each level provides a well-defined list of enumerated items. In order to "address" an event, there is a tuple scheme preferred: "as.exin.dom.dev" for example provides an order in which events should be noted: The first field of the tuple should indicate a value for the actuator/sensor event, the second field should indicate whether the event is coming from an internal or an external device, the third field indicated the content domain, and the fourth field indicates the type of the device.

Along with this event notation, an external medical heart beat sensor event could be addressed e.g. by the tuple 0.1.10.1, with the first 0 indicating that this event is generated by a sensor, the following 1 that it came from an external device, the following 10 indicating the medical domain, the final 1 characterizing a heart rate sensor. According to FIG. 5, the next level indicates that the data the heart beat sensor is providing are heart beat data. On the next level, the type of the data indicated on the forth level is specified. Thus lower level entries can depend on upper level entries. The entry on the lowest level shows that the heartbeat is given on a time basis.

The other event tuple that is depicted in FIG. 5 provides an event delivering sensor data from an internal communication entity that is a scanner. The scanner data indicate that a new device was discovered with its MAC address.

Some or all of such fields can be subject to a hierarchical system of fields. The introduction of fields facilitates filtering events or skipping unknown events.

In addition, there is another two tuple introduced as preferred embodiment that always trails the "address" part: The first tuple selects well-defined data sub-fields, for example, for a medical blood pressure cuff sensor: systolic blood pressure, diastolic blood pressure, heart rate. The second indicates the data type, for example, integer, Boolean, time, date, string, binary. Also, each event can carry with it a universal ID of the adapter that injected it into the event system as well as a timestamp noting the time of injection. An event preferably consists of at least the event header (containing the UID, the event timestamp, and the event address). Optionally it contains sub-fields containing additional data. An adapter/agent can on receipt of an event annotate the received event. If an event is annotated, the event engine will then redistribute that event to all subscribed agents/adapters. Optionally, the original source and the annotated source can be filtered out if bandwidth should be conserved.

Any event notation described above represents an hub internal notation. Thus, adapters have to be aware of the notation used since adapters are responsible for converting an external event notation into the internal one and vice versa. Of course, internal entities in form of agents are also aware of the event notation used since agents process events. In combination with the event notation introduced above, it is for example easily to process events by filtering, such as only evaluating received events that start with a "0.1.10 . . . " in the first three fields and thus only deal e.g. with sensor data from medical sensors. An agent might be specialized in that and have the corresponding procedures available for processing sensor data from medical sensors.

As an example, consider a chest strap that picks up a person's heartbeat and generates a Bluetooth signal for each heartbeat. The adapter on the mobile hub timestamps each heartbeat and the corresponding events would be labeled 0.1.10.1.1.5:

the first digit, 0, indicates that this is a sensor event (and not an actuator command);

the next digit, 1, indicates that the sensor event is provided by an external sensor;

the next digit, 10, indicates that the sensor is a medical sensor;

the next digit, 1, indicates that the sensor is a heart rate sensor;

the next digit, 1, indicates that the heart rate sensor is sensing heartbeats;

the next digit, 5, indicates that the information is the timestamp of a heartbeat.

The benefit of using such a notation is that it is very easy to filter out events that an adapter is not interested in; for example, an adapter that is only interested in external medical sensor events can discard all events that do not have the 0.1.10 prefix; or it could discard information that it does not understand. If, for example, a new sensor would provide not only the timestamp of the heartbeat but also the current averaged rate, it would then be able to pick up the time stamped heartbeat data but just ignore the current average rate data.

The event handling system according to the present invention can preferably implemented on the Linux platform. Events can be stored in shared memory region. Event notifications can be accomplished by Unix System V messaging. Alternatively, the event handling system can be implemented on Symbian's mobile phone operating system. Here events are distributed via object invocation It should be noted that the method of the present invention may be embedded in a program product, which includes all features for implementing the method of the present invention and can implement the method when it is loaded in a machine system.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims.

That which is claimed is:

1. A method for managing events in a mobile hub, the method comprising:
storing an event in a circular buffer;
monitoring a storage period of the stored event in the circular buffer; and
discarding the event from the buffer when the storage period exceeds a time-out; wherein the time-out is a variable time-out that depends on an event arrival rate;
wherein the monitoring further comprises monitoring acknowledgement messages received from entities in response to a notification that was sent to these entities;
wherein the discarding further comprises discarding an event from the buffer when an acknowledgement message was received before the time-out of the timer from each entity notified with regard to this particular event; and else discarding the event from the buffer when the time-out of the associated timer is exceeded and when an acknowledgement message was not received before the time-out of the timer from all the entities notified with regard to this particular event.

2. The method according to claim 1, further comprising notifying registered entities upon the arrival of an event.

3. The method according to claim 2, wherein an entity is an external entity communicating with the mobile hub via a wireless network.

4. The method according to claim 2, wherein an entity is an internal entity of the mobile hub for processing events.

5. The method according to claim 1, further comprising distributing an annotation to registered entities which annotation was received in combination with an acknowledgement message.

6. The method according to claim 1, further comprising distributing an annotation to registered entities which annotation was received in combination with an event.

7. The method according to claim 1, further comprising distributing an event to registered entities which event comprises an annotation attached to the original event.

8. The method according to claim 1, wherein the appearance of an event follows an event notation which notation comprises different fields per event, each field specifying a certain category of information.

9. The method according to claim 8, wherein at least some of the fields follow a hierarchy.

10. A mobile hub comprising:
a circular buffer configured to store sensor values;

a timer configured to monitor the storage period of a sensor value stored in the buffer; and an event manager configured to discard the event from the buffer when a time-out of the associated timer is exceeded, wherein the time-out is a variable time-out that depends on a sensor value arrival rate; and wherein the event manager is further configured to:
- monitor acknowledgment messages received from entities in response to a notification that was sent to these entities;
- discard the sensor value from the buffer when an acknowledgement message was received before the time-out of the timer from each of the entities notified with regard to the sensor value; and
- discard the sensor value from the buffer when the time-out of the associated timer is exceeded and when an acknowledgement message was not received before the time-out of the timer from all the entities notified with regard to the sensor value.

11. The mobile hub according to claim 10, wherein the time-out differs for sensor values associated to different applications.

12. The mobile hub according to claim 10, wherein every sensor value stored in the buffer has an associated timer.

13. The mobile hub according to claim 10, wherein the buffer has a capacity for storing less than 200 sensor values.

14. The mobile hub according to claim 13, wherein the buffer has a capacity for storing less than 100 sensor values.

15. The mobile hub according to claim 10, further comprising an interface to a wireless local area network for receiving and/or transmitting sensor values from/to external entities.

16. The mobile hub according to claim 10, further comprising an interface to a wireless wide area network configured to receive and/or transmit sensor values from/to external entities.

17. The mobile hub according to claim 10, further comprising an adapter configured to convert an internal representation of the sensor value into a representation of the sensor value comprehensible to an external entity and vice versa.

18. The mobile hub according to claim 10, further comprising an internal entity configured to process sensor values.

19. The mobile hub according to claim 10, wherein the event manager is configured to store an arriving sensor value in the buffer and to start the associated timer.

20. The mobile hub according to claim 10, further comprising a registration list configured to identify entities that should be notified at the appearance of the sensor value.

21. The mobile hub according to claim 20, wherein the event manager is configured to notify entities according to the registration list upon the arrival of the sensor value.

22. A computer program product for managing events in a mobile hub, the computer program product comprising:
- a computer usable storage medium having computer usable program code embodied therewith, the computer usable program code configured to:
- store an event in a circular buffer;
- monitor a storage period of the stored event in the circular buffer; and
- discard the event from the buffer when the storage period exceeds a time-out; wherein the time-out is a variable time-out that depends on an event arrival rate,
- wherein the monitoring further comprising monitoring of acknowledgement messages received from entities in response to a notification that was sent to these entities; and
- wherein the discarding further comprising discarding an event from the buffer when an acknowledgement message was received before the time-out of the timer from each entity notified with regard to this particular event; and else discarding the event from the buffer when the time-out of the associated timer is exceeded and when an acknowledgement message was not received before the time-out of the timer from all the entities notified with regard to this particular event.

* * * * *

UNITED STATES PATENT AND TRADEMARK OFFICE
CERTIFICATE OF CORRECTION

PATENT NO. : 7,757,019 B2 Page 1 of 1
APPLICATION NO. : 11/420473
DATED : July 13, 2010
INVENTOR(S) : Dirk Husemann et al.

It is certified that error appears in the above-identified patent and that said Letters Patent is hereby corrected as shown below:

On the cover page, insert:

--(30) Foreign Application Priority Data
Nov. 25, 2003    (EP) ………………………. 03405843.8--

Signed and Sealed this

Twenty-first Day of December, 2010

David J. Kappos
*Director of the United States Patent and Trademark Office*